United States Patent [19]
Rani et al.

[11] Patent Number: 5,634,907
[45] Date of Patent: Jun. 3, 1997

[54] SYSTEM FOR DETECTION OF FLUID INFUSION

[75] Inventors: Robert G. Rani, Roseville; Lester D. Michels, Maple Grove, both of Minn.

[73] Assignee: Sandoz Nutrition Ltd., Berne, Switzerland

[21] Appl. No.: 363,192

[22] Filed: Dec. 22, 1994

[51] Int. Cl.$^6$ ............................................. A61M 1/00
[52] U.S. Cl. ........................ 604/151; 604/153; 604/50; 128/DIG. 12; 128/DIG. 13
[58] Field of Search ................. 128/DIG. 12, DIG. 13; 604/151–153, 50, 67, 254, 131, 251, 253

[56] References Cited

U.S. PATENT DOCUMENTS

| | | |
|---|---|---|
| 4,217,993 | 8/1980 | Jess et al. . |
| 4,758,228 | 7/1988 | Williams . |
| 4,913,703 | 4/1990 | Pasqualucci et al. . |
| 5,147,313 | 9/1992 | Dikeman . |
| 5,181,842 | 1/1993 | Sunderland et al. . |
| 5,219,327 | 6/1993 | Okada . |
| 5,374,251 | 12/1994 | Smith . |

*Primary Examiner*—Robert A. Hafer
*Assistant Examiner*—Perry E. Van Over
*Attorney, Agent, or Firm*—Robert S. Honor; Carl W. Battle; Gabriel Lopez

[57] ABSTRACT

An infusion apparatus includes a pump and a fluid delivery set. The infusion apparatus is adapted to monitor the fluid delivery set for insuring proper placement in relation to the pump. The infusion apparatus further includes a sensor which operates to detect the proper alignment of the fluid delivery set and also the proper operating position of the infusion apparatus. The infusion apparatus includes a cover which is adapted to be in a closed position when the infusion apparatus is in proper operating position. The cover operates to secure the fluid delivery set within the mounted position in the infusion apparatus.

14 Claims, 7 Drawing Sheets

5,634,907

SYSTEM FOR DETECTION OF FLUID INFUSION

BACKGROUND OF THE INVENTION

1. Field of the Invention

The present invention relates generally to infusion systems for administering fluids intravenously or enterally and more particularly to infusions systems capable of monitoring intravenous or enteral fluid delivery for safety of the patient.

2. Description of the Prior Art

Infusion systems generally are comprised of a mechanical pump and an arrangement of flexible tubing that is adapted for delivering fluid enterally or intravenously, for example a nutritional or medicinal product. For this purpose, the flexible tubing is mountable on the pump and connected between a fluid source and the patient. In operation, the pump is specifically regulated in order to deliver the fluid through the flexible tubing and to the patient. Ordinarily, the particular arrangement of flexible tubing utilized is manufactured either for being reusable or otherwise made disposable after a single use.

One well known example of mechanical pump which is commonly utilized for infusion systems are peristaltic pumps. Peristaltic pumps are typically used with disposable tube arrangements, generally referred to as fluid delivery sets or cartridges. Fluid delivery sets essentially consist of a storage container for holding the fluid product, a drip chamber connected to the storage container by a fluid tube, and a set adapter which is connected to the drip chamber by an inlet tube on one end and to the patient via an outlet tube on its second end. Peristaltic pumps are typically comprised of two members, a housing and a door. The housing essentially holds a motor driven rotor and is also adapted to mount the fluid delivery set on assembly. For this purpose, the housing is usually provided with a series of apertures arranged within its outer surface onto which the fluid delivery set is mounted. In particular, the drip chamber and set adaptor are each usually mountable within the housing apertures for retaking the fluid delivery set. The door is connected to the housing and is adapted to secure and conceal the fluid delivery set in its mounted position when closed against the housing. The rotor which is also mounted on the outer surface of the housing is included with a series of rollers through which a portion of the fluid tubing of the fluid delivery set is positioned. As the rotor is driven by the motor, the rollers are adapted to compress the portion of flexible tubing extending therethrough which operates to pass the fluid within the tube. In this manner, the rate of rotation of the rotor is regulated in order to adjust the rate of fluid delivery to the patient.

One problem however which has been observed with prior arc infusion devices is the inability to insure safe fluid delivery to the patient. In particular, with numerous infusion systems it is possible for the fluid delivery set to be improperly mounted on the pump or otherwise become dislodged from its mounted position on the pump housing during fluid delivery. In situations where this would occur, the fluid delivery could either terminate or result with an uncontrolled "free" flow of fluid to the patient, thus creating a potentially hazardous situation. Furthermore, with these and other such infusion systems there is no manner provided in order to regulate the specific type of fluid delivery set being utilized. For example, the operating parameters of a particular pump when utilized within an infusion system could be dependent on the characteristics of a specific fluid delivery set, for instance, one including a predefined size or length of fluid tubing or arrangement of individual components. Furthermore, a particular fluid product which is required by a patient may only be obtainable through use of a specific fluid delivery set. In this situation, unintentional use of a different fluid set containing another type of fluid could potentially be critical to the patient.

Because of these and other problems associated with infusion systems presently employed, there now exists a need for an improved infusion system capable of safely delivering fluid enterally or intravenously to a patient.

SUMMARY OF THE INVENTION

The present invention provides an infusion system adapted for enteral or intravenous delivery of fluids. In accordance with the present invention, a system for monitoring the delivery of fluid to a patient is provided. For this purpose, the system includes a pumping means and a fluid delivery set. The fluid delivery set is connectable in a predetermined position on the pumping means for delivering the fluid to the patient. The pumping means enables delivery of the fluid and includes as portions thereof a housing and a retaining member. The retaining member of the pumping means includes a closed and an open position relative to the housing. The pumping means also includes means for monitoring the fluid delivery set. For this purpose, the monitoring means includes means for detecting at least a section of the fluid delivery set when the fluid delivery set is in the predetermined position on the pumping means and the retaining member of the pumping means is in the closed position relative to the housing.

The present invention also provides a method of mounting a fluid delivery set onto a pump for monitoring delivery of fluid to a patient. For this purpose, the fluid delivery set includes at least a first mounting member of a predefined geometry and the pump includes a housing and a closure. The closure includes a closed and an open position relative to the housing. The housing further includes a rotor for controlling delivery of the fluid, a recess and a sensor substantially adjacent the recess. The sensor includes an actuated and a non-actuated state and the rotor receives a portion of the fluid delivery set. In accordance with the present invention, the method comprises the step of installing said first mounting member of the fluid delivery set in a predetermined position in the recess provided on the housing. The method further comprises the step of providing the closure in the closed position relative to the housing wherein the closure displaces said first mounting member of the fluid delivery set in a direction of the sensor which causes a change in state of the sensor from the non-actuated to the actuated state.

In accordance with the present invention, an object is to provide an improved infusion pump for delivery of fluids enterally or intravenously to a patient.

Another object of the present invention is to provide an infusion pump adapted for monitoring the enteral or intravenous delivery of fluids through a continuous arrangement of tubing for safety of the patient.

It is still another object of the present invention to provide an infusion pump adapted for detecting improper assembly of the continuous tubing arrangement or where a wrong tubing arrangement has been utilized with the infusion pump.

Yet another object of the present invention is to provide an infusion pump adapted for detecting occurrences where the continuous tubing arrangement is dislodged from its assembled position or otherwise not present within the infusion pump.

These and other objects of the present invention will become more readily apparent when taken into consideration with the following description and the attached drawings.

DETAILED DESCRIPTION OF THE PREFERRED EMBODIMENTS

Figure 1:
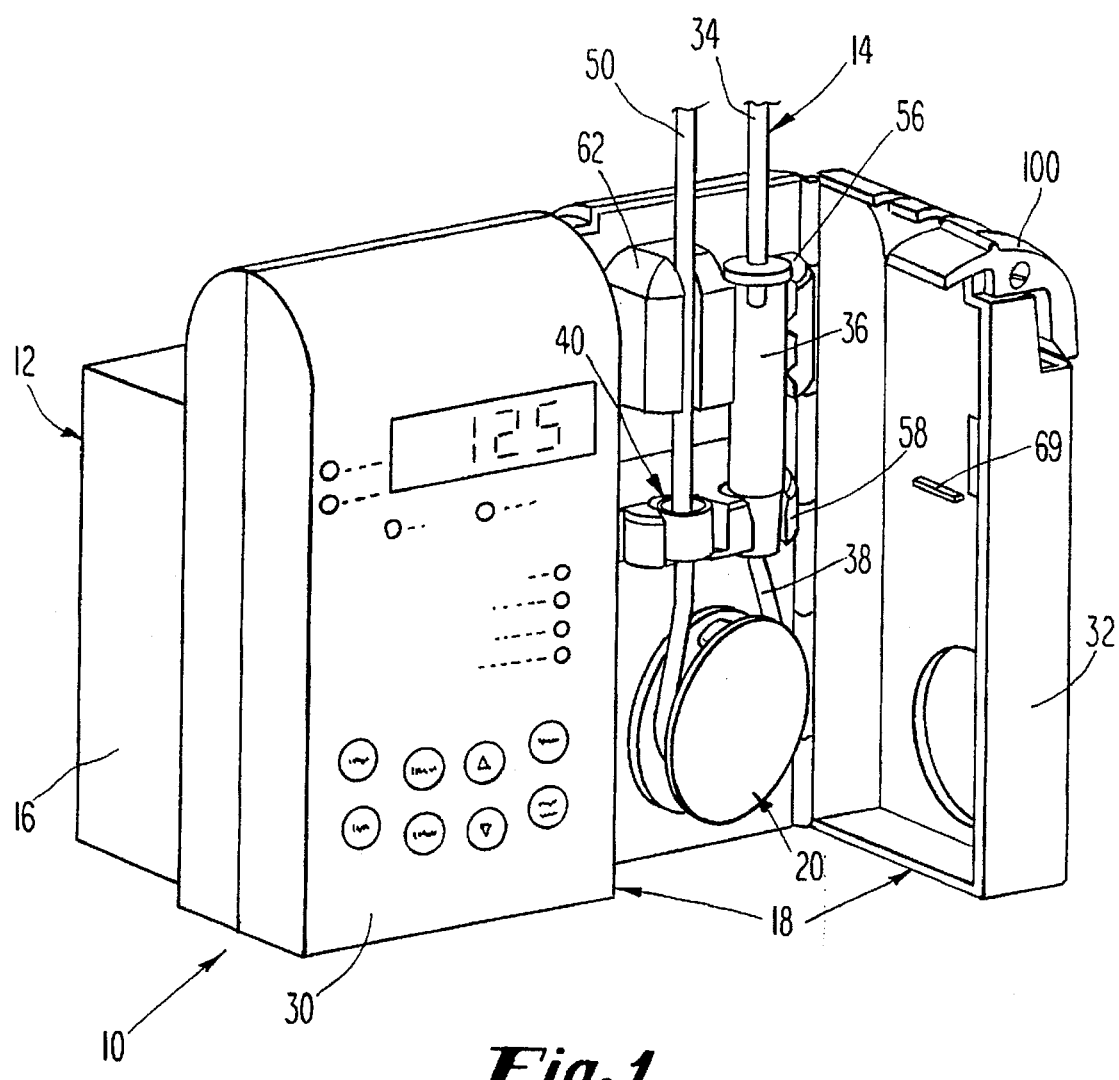
FIG. 1 is a perspective view of an infusion pump assembly according to the present invention, the infusion pump assembly being shown in an open position.
Figure 2:
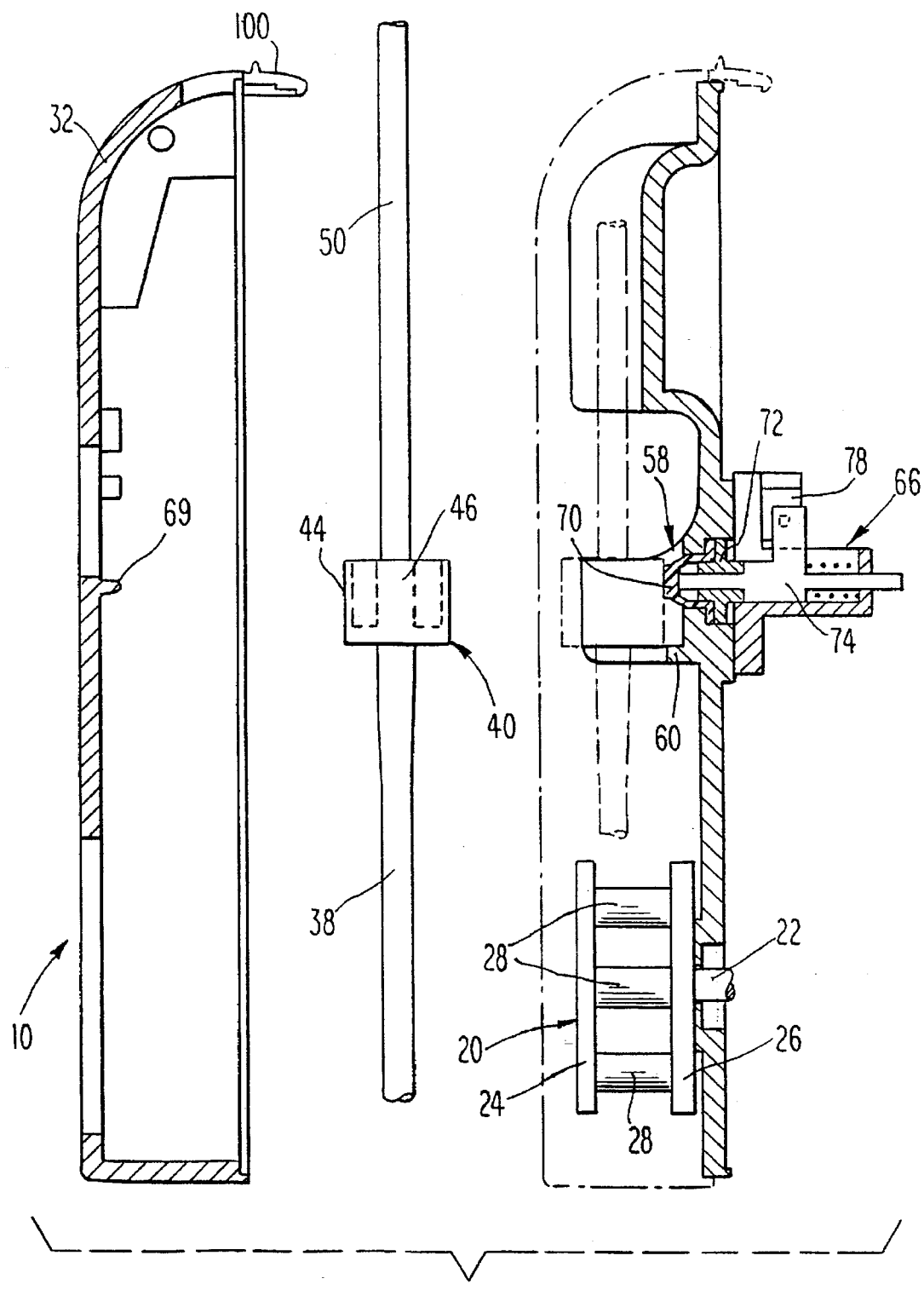
FIG. 2 is an exploded sectional elevational view of the infusion pump assembly of FIG. 1, the infusion pump assembly of FIG. 2 further illustrating in phantom a set adaptor in a mounted position.

Referring now to the drawings in detail, wherein like reference numerals indicate like elements throughout the several views, there is shown in FIG. 1 a perspective view of an infusion pump assembly 10 in accordance with the present invention. The infusion pump assembly 10 as shown includes, as portions thereof, a pumping means comprising a pump 12 and a fluid delivery set 14. In the present embodiment, the pump 12 is a rotary type peristaltic pump, however it should be understood that any type of pump can be provided for this same purpose. The pump 12 as illustrated comprises a housing 16 and a retaining member or closure 18. The housing 16 comprises a generally rectangular member which is adapted to contain and support the various components comprising the infusion pump assembly 10. In the present embodiment, the housing 16 includes a rotor 20 which is provided on its front outer surface and in connection with a pump motor (not shown). The rotor 20 includes a rotor shaft 22, as is best seen in FIG. 2, which extends through an opening provided through the front of the housing 16 for connection with the pump motor. In operation, the pump motor is adapted to provide rotation of the rotor 20 at various rates via the rotor shaft 22 for delivering a source of fluid (not shown), for example, an enteral fluid. As is best shown in FIG. 2, the rotor 20 of the present invention includes a pair of oppositely situated, substantially spherical flanges 24 and 26 connected by three equally spaced rollers 28. The rollers 28 are each mounted on a pin, preferably of metal, which extend between the two opposing flanges 26 and 28 and which allow the rollers 28 to rotate during the operation recited above.

As is shown in FIG. 1, the closure 18 is comprised of a pair of cover members 30 and 32. In the present embodiment, the first cover member 30 is mounted onto the front outer surface of housing 16 and the second cover member 32 is pivotally coupled by means commonly known in the art to the housing 16 adjacent an end thereof. As is illustrated in the figures, the second cover member 32 is adapted to be rotated between an open position shown in FIG. 1 and a closed position shown in FIG. 3. The first cover member 30 is adapted to house a control and display panel, such as that shown in FIG. 1, which operates to regulate and monitor the operation of the infusion apparatus 10. The second cover member 32 or the housing 16 has a latching mechanism 100 or equivalent means for maintaining cover member 32 in a closed position.

Figure 5:
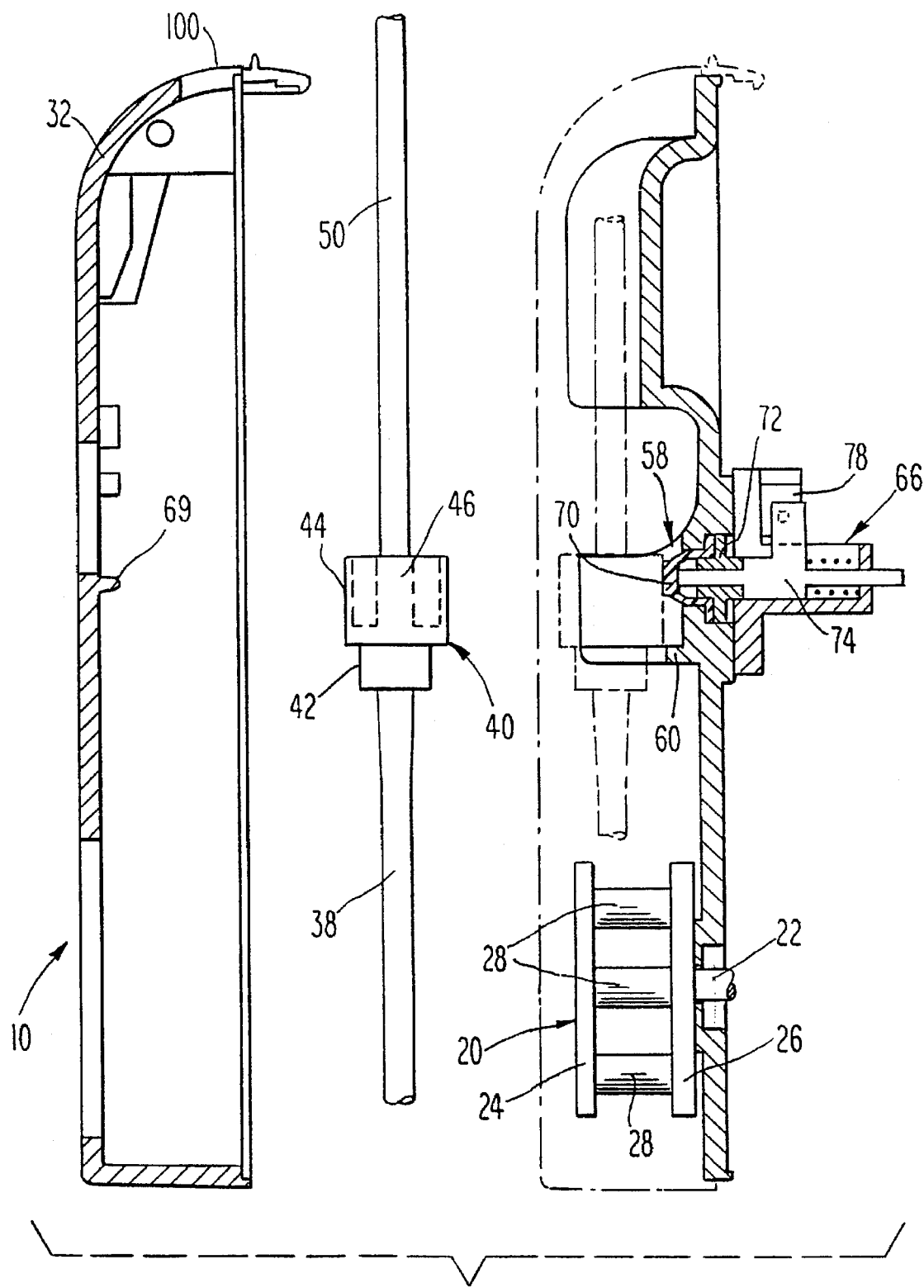
FIG. 5 is an exploded sectional elevational view of the infusion pump assembly of FIG.. 4, the infusion pump assembly of FIG. 5 further illustration in phantom a set adaptor in a mounted position.
Figure 6:
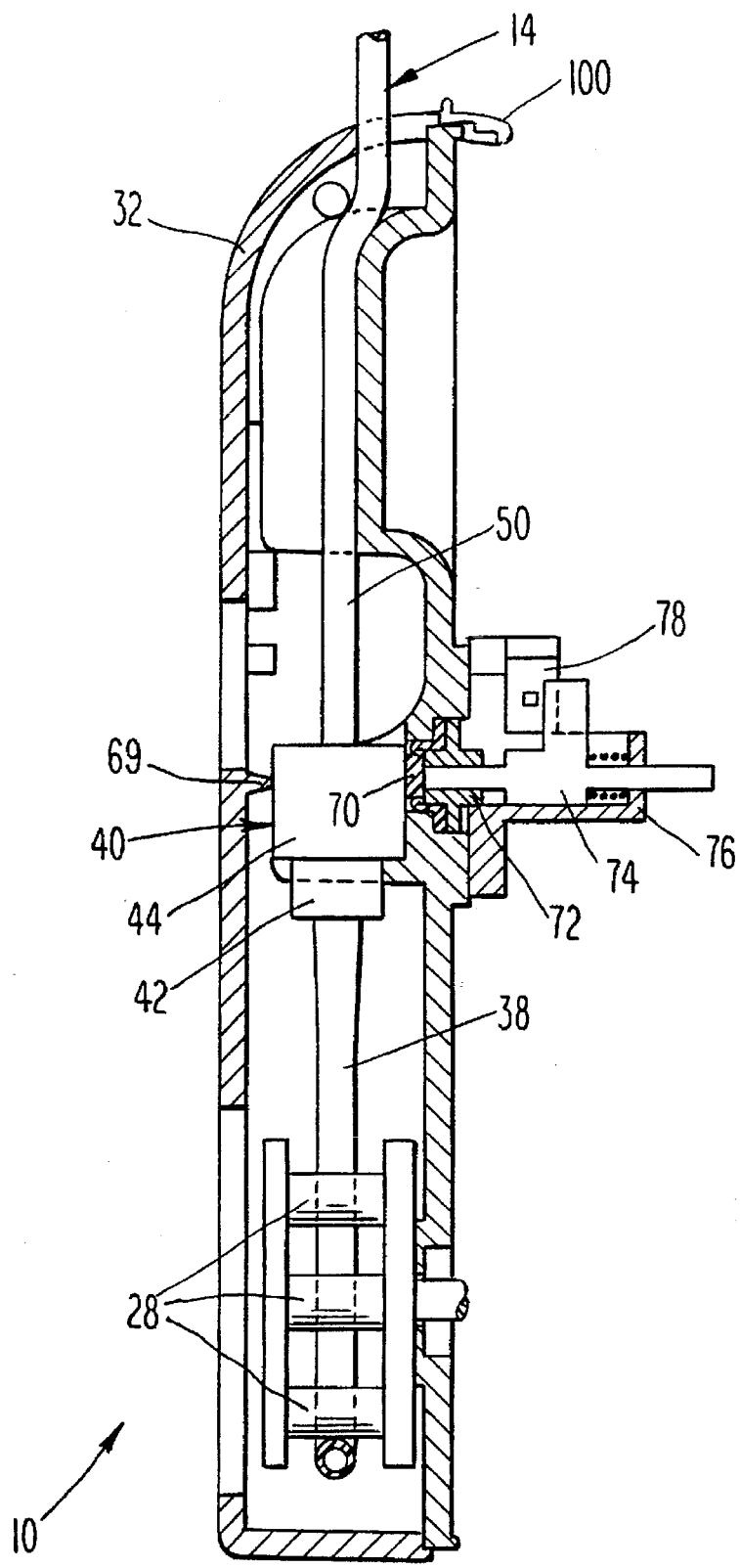
FIG. 6 is a sectional elevational view of the infusion pump assembly of FIG. 4 being shown in a closed position.
Figure 7:
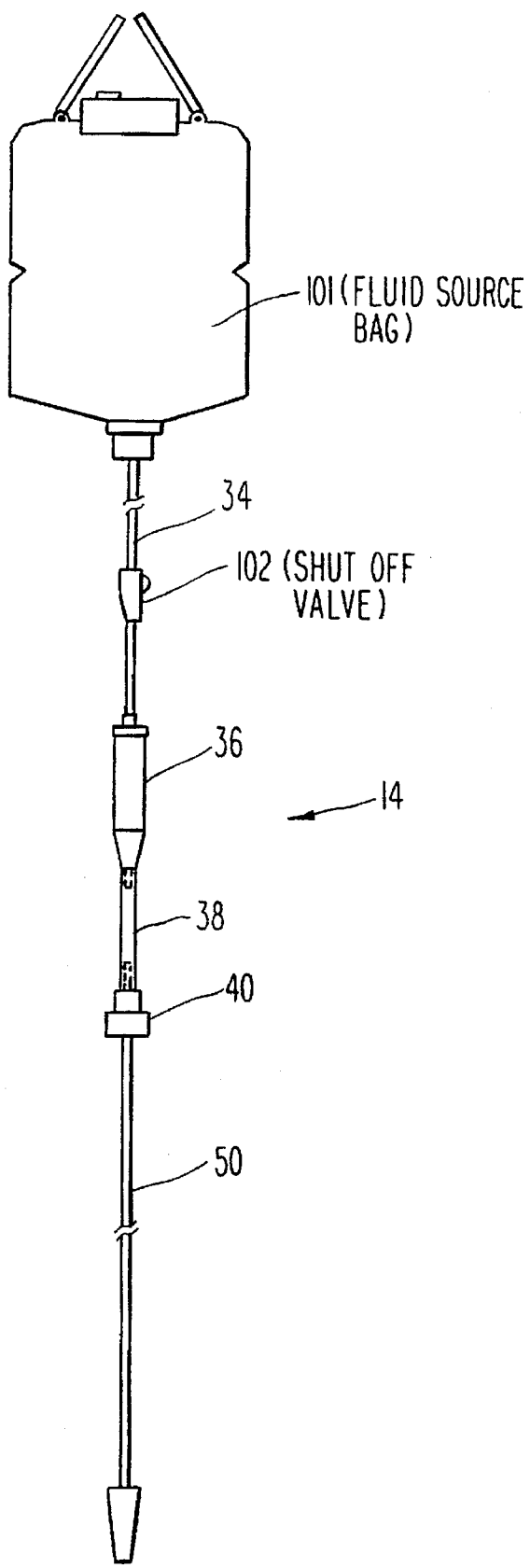
FIG. 7 is an elongated view of a fluid delivery set for use with an infusion pump assembly according to the present invention.
Figure 8:
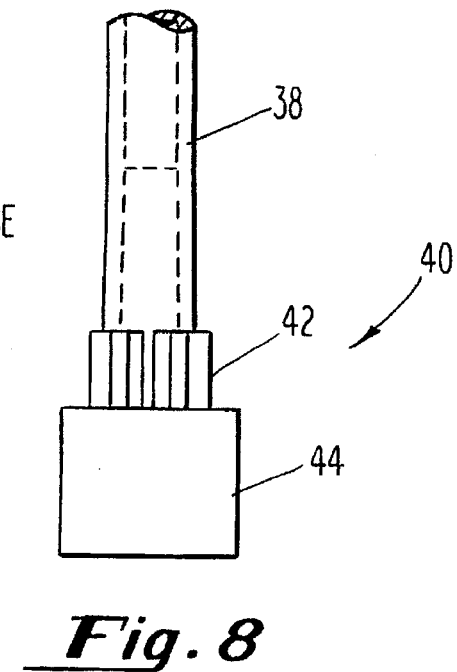
FIG. 8 is an elevational view of a set adapter useful with an infusion pump assembly according to the present invention.
Figure 9:
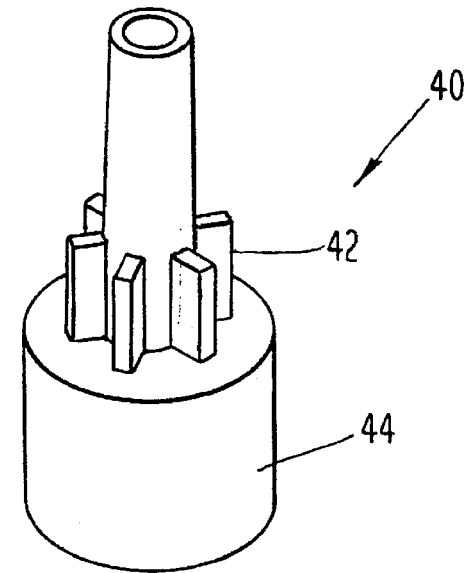
FIG. 9 is perspective view of a set adapter useful with an infusion pump assembly according to the present invention.

The fluid delivery set 14 as illustrated is mounted to the front outer surface of the housing 16 in the manner shown in FIG. 1. The fluid delivery set 14 according to the present invention essentially comprises a conventional disposable fluid delivery set or cassette, however it should be understood that the present invention can also be adapted for use with reusable fluid delivery arrangements. The fluid delivery set 14 as shown includes a generally elongated flexible inlet tube 34, which at one end is connected to the fluid source and to an inlet of a drip chamber 36 at its second end. The drip chamber 36 in the present embodiment comprises a generally elongate member having a cylindrical-shaped first portion and a cone-shaped tapered second portion, however other configurations can also be provided for this same purpose. The first and second portions are each generally hollow members in order for receiving the fluid source therein on operation. Preferably, the drip chamber 36 is manufactured of a substantially rigid and transparent material, such as from thermoplastic or thermosetting materials. The cylindrical-shaped first portion also includes a stopper member which is fastened to the inlet thereof. The engagement of the stopper member and the cylindrical-shaped first portion provides an annular flange as part of the stopper member. A second annular flange is formed as part of the cylindrical-shaped first portion at the point of engagement with the cone-shaped tapered second portion. The free end of the cone-shaped tapered second portion is connected to a first end of a tube member 38, preferably consisting of a resilient and compressible material, such as silicone. The second end of the tube member 38 is connected to a first end of a mounting member or set adaptor 40. In accordance with the present invention, the set adaptor 40 can be of any defined configuration or shape. In one embodiment, the set adaptor 40 as illustrated in FIG. 2 primarily includes cylindrical member 44. In a preferred embodiment, the set adaptor 40 as illustrated in FIG. 8 and FIG. 9 primarily includes two adjoining cylindrical members 42 and 44. The diameter of the second member 44 as shown is greater than that of the first member 42, thereby forming a flange at the connection therebetween. In this embodiment, the second cylindrical member 44 is also included with a correspondingly configured cylindrical cavity as shown in dotted line in FIG. 5 provided within its upper surface distal the first member 42. As best seen in FIG. 5, the set adaptor 40 further includes a third cylindrical member 46 extending from the area of the flange and positioned within the cavity of the second member 44. As best illustrated in FIG. 5, each of the members 42, 44, and 46 are included with aligned cylindrical-shaped channels therein that are adapted to provide a continuous passage for the fluid through the set adaptor 40. Similar to the drip chamber 36, the composition of the set adaptor 40 can also be of standard thermoplastic or thermosetting materials. Furthermore, as illustrated in the FIGS., the second end of the set adaptor 40 is provided in connection with a first end of an outlet tube 50. The outlet tube 50 as shown is generally an elongated flexible tube member which is adapted to deliver the fluid product from the infusion pump assembly 10 and to the patient.

Figure 4:
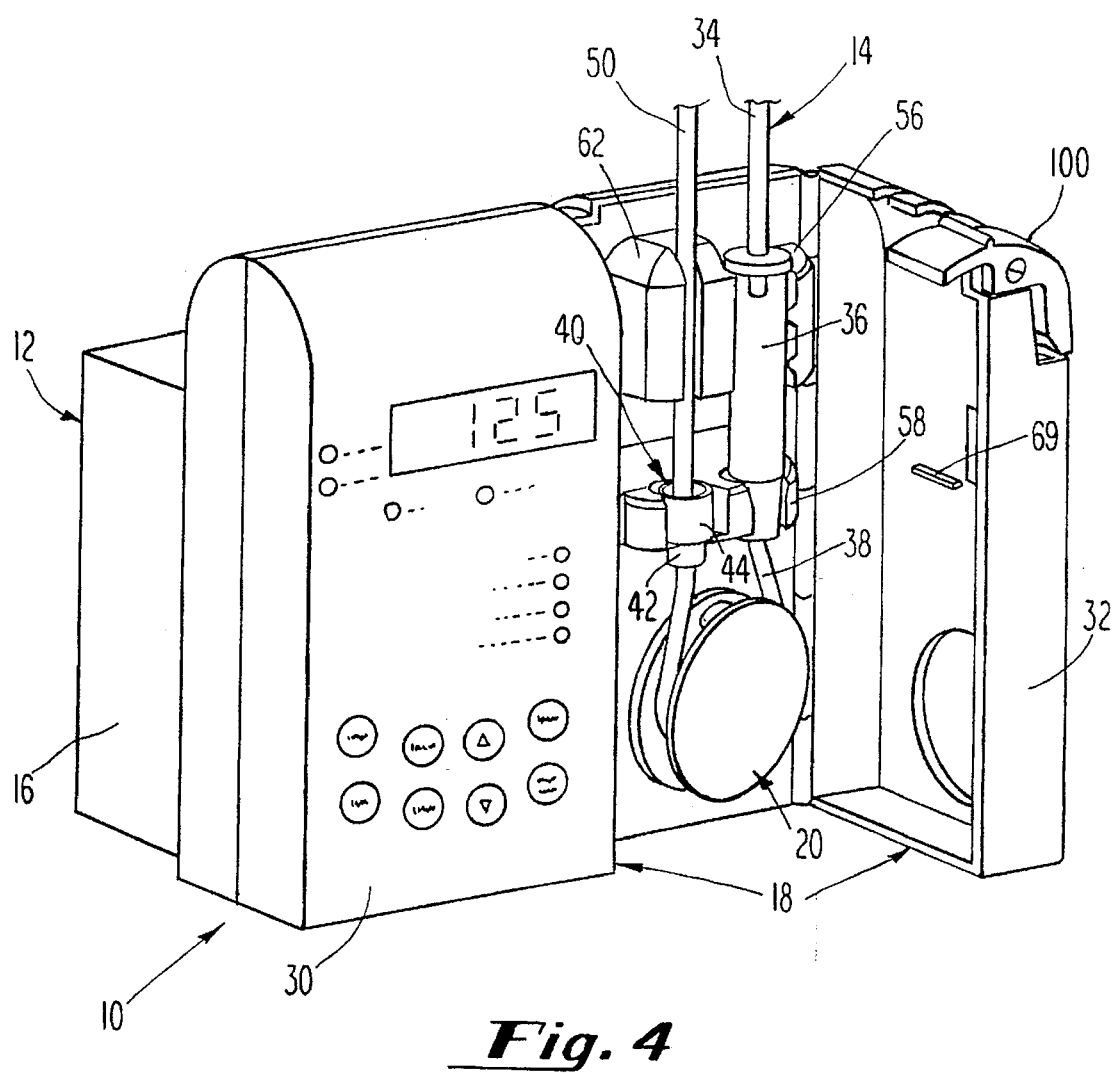
FIG. 4 is a perspective view of another embodiment of an infusion pump assembly according to the present invention shown in an open position having a set adaptor comprising cylindrical member (44) and (42)

As indicated above, the fluid delivery set 14 is adapted to be mounted to the housing 16. For this purpose, the fluid delivery set 14 is mountable to the front outer surface of the housing 16 in the manner illustrated in the figures. As best seen in FIG. 1 and FIG. 4, the housing 16 is included with portions 56 and 58 extending from the front outer surface as shown. The portions 56 and 58 are in turn provided with a pair of drip chamber receiving recesses therein of the configuration shown. In this manner, the cylindrical-shaped first portion of the drip chamber 36 is receivable within the recess provided in the portion 56 and the cone-shaped tapered second portion of the drip chamber 36 is receivable within the recess provided in the portion 58. Furthermore, the portion 58 is further provided with a set adaptor receiving aperture therein of the configuration shown. In the present embodiment, the drip chamber receiving recess and adjacent set adaptor receiving aperture of portion 58 are each substantially radiused in configuration. The portion 58 as best shown in FIG. 2 and FIG. 5 is further included with a substantially radiused seating member 60 formed as part of the set adaptor receiving aperture. On mounting, the set adaptor 40 as illustrated is seated by the flange provided at the intersection of the cylindrical member 44 and tube 38 or cylindrical members 42 and 44 within the seating member of the set adaptor receiving aperture. The cylindrical member 44 extends from the seating member and is positioned substantially within the set adaptor receiving aperture for a purpose to be hereinafter described. As best seen in FIG. 1 and FIG. 4, the housing 16 is further included with a third portion 62 extending outwardly from its front outer surface adjacent the portion 56. The third portion 62 as shown is included with a cylindrical shaped channel extending therethrough which receives the outlet tube 50. The tube member 38 is positioned around the rotor 20 and in contact with the rollers 28. On operation, the rotation of the rollers 28 operate to pass the fluid through the fluid delivery set 14 in accordance with conventional rotor devices.

Figure 3:
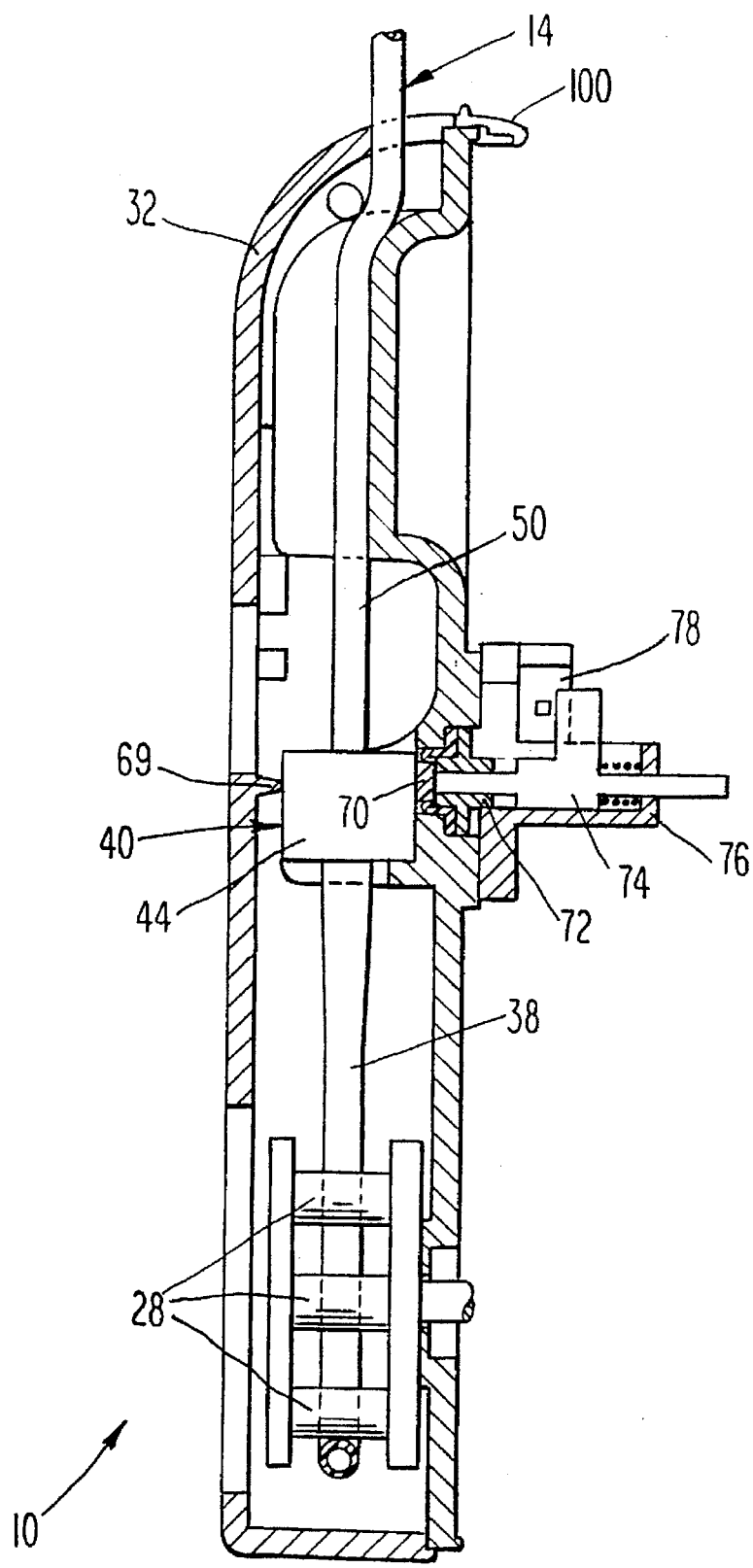
FIG. 3 is a sectional elevational view of the infusion pump assembly of FIG. 1 being shown in a closed position.

In accordance with the present embodiment, the housing 16 further includes a sensor 66 mounted therein in order for detecting the proper placement of the set adaptor 40 in relation to the set adaptor receiving aperture in portion 58. As illustrated in the figures, the housing 16 is included with a generally cylindrical aperture provided through its front outer surface through which the sensor 66 is mounted. Preferably, the sensor 66 is arranged within housing 16 in the manner described below in order to detect the set adaptor 40 when properly received within the set adaptor receiving aperture. As best seen in FIGS. 2 and 3, the sensor 66 for this purpose is mounted adjacent the set adaptor receiving aperture of portion 58 as shown.

As best illustrated in FIG. 1, the second cover member 32 of the closure 18 is a generally rectangular member having an outer surface and an inner surface. The inner surface of the second cover member 32 as shown includes a cavity formed therein which defines an inner cavity surface. In the present embodiment, the inner cavity surface is adapted to enclose the fluid delivery set 14, the rotor 20 and the projecting portions 56, 58 and 62 when the second cover member 32 is in its closed position. Preferably, a substantially cylindrical recess is further provided within the second cover member 32 through which the rotor 20 is visible when in the closed position shown in FIGS. 2 and 3. In accordance with the present embodiment, a generally elongated boss 69 can further be provided projecting outwardly from the inner surface of the cover member 32, however it should be understood that same is optional. In this arrangement, the generally elongated boss 69 is adapted to engage the set adaptor 40 as the cover member 32 is moved into the closed position, as is shown in FIG. 3. Otherwise, the inner surface of cover member 32 would directly engage the set adaptor 40. As is shown in FIG. 3, the first and second cover members 30 and 32 are each preferably adapted to be substantially contiguous with each other when the cover member 32 is rotated to its closed position. The second cover member 32 is further provided with a pair of adjacent apertures provided within its upper surface through which extend the two tubing portions 34 and 50 when the cover member 32 is in the closed position. As best illustrated in FIG. 4, the cover member 32 has a latch mechanism 100 for holding the cover member 32 in a closed position.

In the present embodiment, the sensor 66 is illustrated comprising a retractable sensor member comprising a plunger boot 70 which extends through the opening of the housing 16, a spring biased plunger 74 which extends within the plunger boot 70, a plunger barrel 76 which receives the plunger 74, a detector 78, such as a photodetector disposed on the plunger barrel 76 and a plunger retainer 72 for securing the foregoing within the aperture of the housing 16. As best seen in FIGS. 2 and 3, the set adaptor 40, via the second member 44, when mounted in the set adaptor receiving aperture is adapted to be positioned in engagement with the plunger 74 for the purpose described below.

As previously described, an important feature of the present invention is to insure proper placement of the fluid delivery set 14 relative to the housing 16. As to the drip chamber 36, proper positioning and alignment is regulated since it must engage both recesses of portions 56 and 58 of the housing 16. As to the set adaptor 40, as indicated above, the sensor 66 operates to insure proper positioning and alignment on the housing 16. In accordance with the present invention, the sensor 66 preferably is adapted to detect instances when the set adaptor 40 is not correctly positioned within the set adaptor receiving aperture and also when the second cover member 32 is not in the closed position relative to the housing 16. As illustrated in the figures, the details of one arrangement for this purpose is shown. In the present embodiment, as best illustrated in Phantom in FIG. 2, the sensor 66 when the second cover member 32 is in an open position is provided in an extended position, which displaces the set adaptor 40 forward and into the front portion of the set adaptor aperture. As the second cover member 32 is closed to the position illustrated in FIG. 3, the boss 69 is first adapted to engage and then displace the set adaptor 40 backwards and in the direction of the front outer surface of the housing 16, which operates to compress the plunger 74 into the retracted position shown. In this embodiment, the sensor 66 is adapted to be in an actuated state when the plunger 74 is in the retracted position of FIG. 3, and in a non-actuated state when in the extended position illustrated in phantom in FIG. 2.

In accordance with the illustrated embodiment, the detector 78 is adapted to provide an output signal depending on whether the sensor 66 is in the actuated or non-actuated state. For instance, by way of example, the photodetector as shown can be of a type to provide an output of +5 volts when the plunger 74 is in the extended position, which corresponds to the non-actuated state of the sensor 66, and 0 volts when the plunger 74 is in the retracted position of FIG. 3, corresponding to the actuated state of the sensor 66. The output signal of the detector 78 is monitored in order to detect the state of the sensor 66 corresponding to the positioning of the set adaptor 40. As indicated earlier, the infusion pump assembly 10 is preferably adapted to detect when the set adaptor 40 is not properly positioned within the set adaptor aperture and when the second cover member 32 is not provided within the closed position, which corresponds to occurrences where the sensor 66 is in the non-actuated state, with the plunger 74 in the extended position. For this purpose, the present embodiment further includes an alarm preferably on the panel of cover member 30 and in connection with the detector 78 which is adapted for being actuated when the sensor 66 is in the non-actuated state. In the present embodiment, an audio and/or visual alarm can be provided for this purpose. In addition, the detector 78, can also be provided in connection with a microprocessor (not shown) which receives the output signal of the detector 78. The microprocessor in turn being connected to the alarm and adapted to cause the alarm to be actuated in response to the non-actuated state of the sensor 66. The microprocessor can also be adapted for other functions, such as to terminate pump operation or otherwise shut down the unit in response to the detected state of the sensor 66.

In view of the foregoing, it will be understood that an advantage of the present invention is to provide an infusion pump assembly adapted to provide an improved mounting of the fluid delivery set. In particular, the housing 16 of the pump 12 includes a specific arrangement of recesses through its portions 56 and 58 on its outer surface which receive the fluid delivery set in a predefined arrangement. Furthermore, the fluid delivery set is secured in this predetermined arrangement by the second cover member 32 when closed against the housing 16.

Furthermore, still another advantage is that the present invention is adapted to monitor the fluid delivery set in order to insure proper attachment to the housing. In particular, the set adaptor 40 is adapted to actuate the sensor 66 when the set adaptor 40 is properly positioned within the set adaptor receiving aperture and the second cover member 32 is closed against the housing 16. In instances where the sensor 66 is not actuated, the infusion apparatus is adapted to actuate an alarm or terminate operation in order to notify the operator of such condition. For example, the set adaptor 40 can be moved within or dislodged from the corresponding aperture, such as from an external impact, which would allow the sensor 66 to undergo a change in state from the actuated to the non-actuated position. Further, a wrong configuration of set adaptor, such as not comprising the particular configuration of set adaptor 40, or when the fluid delivery set is not mounted within the infusion apparatus would result in the sensor 66 being in the non-actuated state. In addition, in instances where the second closure member 32 is not in the closed position against the housing 16, this would also result with the sensor 66 being in the non-actuated state. As mentioned previously, any occurrence of such described above could have very severe implications to a patient.

It will be recognized by those skilled in the an that changes may be made by the above-described embodiments of the invention without departing from the broad inventive concepts thereof. For example, it should be understood that the present invention can be adapted for use in connection with any particular type of fluid delivery systems, such as enteral delivery pumps, intravenous fluid delivery pumps or circulation type pumps, such as blood infusion pumps and dialysis pumps.

Furthermore, while the present invention has been described with reference to a sensor of the plunger type and including a photodetector, it should be understood that other arrangements could also be utilized for the same purpose, such as an optical sensor, magnetic sensor, mechanical switch sensor or pressure sensor. In addition, while the cover member 32 is illustrated as being pivotally coupled to the housing 16, it should be understood that any type of coupling arrangement of the cover member 32 could also be used for the same purpose. Furthermore, in other instances, the cover member 32 could also be provided as a separate member, apart from the housing 16, which is adapted to be connected to the housing 16 on operation.

It is understood, therefore, that this invention is not limited to the particular embodiments disclosed, but it is intended to cover all modifications which are within the scope and spirit of the invention as defined by the appended claims.

We claim:

1. A method of mounting a fluid delivery set onto a pump for monitoring delivery of fluid to a patient, the fluid delivery set having at least a first mounting member of a defined geometry and said pump including a housing and a closure, with said closure having a closed and an open position relative to said housing, said housing further including a rotor for controlling delivery of said fluid, a recess and a sensor substantially adjacent said recess, said sensor of said housing having an actuated and non-actuated state, and said rotor of said housing receiving a portion of said fluid delivery set, the method comprising:

installing said at least a first mounting member of said fluid delivery set in a predetermined position in the recess of said housing; and providing said closure in the closed position relative to said housing wherein said closure displaces said at least a first mounting member of said fluid delivery set in a direction of said sensor which causes a change in state of said sensor from the non-actuated to the actuated state.

2. A method according to claim 1, further including the step of providing an alarm means in communication with said sensor, wherein said alarm means is adapted to be actuated when said sensor is in the non-actuated state.

3. An infusion apparatus comprising:

a pump having a housing and a closure, with said housing including a rotor, at least one recess and a sensor having an actuated and a non-actuated state, said closure being operatively coupled to said housing and adapted to be pivoted between an open and a closed position relative to said housing;

a fluid delivery set mountable on said pump, said fluid delivery set including a tubing section adapted to be received about said rotor and at least a first mounting member of a predefined geometry receivable in a predetermined position within the at least one recess of said housing; and said sensor being responsive to said at least a first mounting member of said fluid delivery set relative to said at least one recess of said housing for monitoring delivery of fluid through said infusion apparatus, wherein when said at least a first mounting member is in the predetermined position within said at least one recess, said closure when pivoted to the closed position relative to said housing is adapted to engage and displace a predetermined amount said at least a first mounting member in a first direction and into a secured position within said recess which causes a change in state of said sensor from the non-actuated to the actuated state, whereby subsequent displacement of said at least a first mounting member a predetermined amount from the secured position in a second or third direction substantially perpendicular the first direction causes a change in state of said sensor from the actuated to the non-actuated state, and whereby subsequent pivotal movement of the closure from the closed position to the open position results in displacement of said at least a first mounting member a predetermined amount from the secured position in a fourth direction generally opposite the first direction which causes a change in state of said sensor from the actuated to the non-actuated state.

4. An infusion apparatus according to claim 3, wherein said sensor comprises a biased sensing member, whereby said at least a first mounting member is adapted to compress said biased sensing member from a substantially extended position to a substantially retracted position as said closure is pivoted to the closed position which causes the change in state of said biased sensing member from the non-actuated to the actuated state.

5. An infusion apparatus according to claim 4, wherein said mounting member comprises a set adapter having a shoulder portion adapted for engaging and compressing said biased sensing member into the retracted position when said closure is pivoted to the closed position.

6. An infusion apparatus according to claim 4, wherein said biased sensing member is adapted to undergo expansion from the substantially retracted position to the substantially extended position as said closure is pivoted from the closed position to the open position which causes a change in state of said biased sensing member from the actuated to the non-actuated state, whereby said expansion of said biased sensing member is adapted to displace said at least a first mounting member the predetermined mount in the fourth direction generally opposite the first direction.

7. An infusion apparatus according to claim 3, wherein said closure includes an inner side having a generally elongate boss projecting outwardly therefrom adapted for engaging and displacing said at least a first mounting member when said closure is pivoted to the closed position.

8. An infusion apparatus according to claim 3, wherein said sensor is provided proximate said at least one recess of said housing.

9. An infusion apparatus according to claim 3, wherein said housing further includes an alarm means in communication with said sensor, wherein said alarm means is adapted to be actuated when said sensor is in the non-actuated state.

10. An infusion apparatus according to claim 3, wherein said housing further includes operating means in communication with said sensor, wherein said operating means enables said pump to rotate said rotor to deliver fluid to a patient when said sensor is in its actuated state.

11. An infusion apparatus according to claim 3, wherein said fluid delivery set further includes a second mounting member and said housing of said pump further includes at least a second recess adapted for receiving said second mounting member.

12. A fluid delivery set for mounting on a pump comprising a tubing section and at least a first mounting member of a predefined geometry;
    wherein said pump has a housing and a closure, with said housing including a rotor, at least one recess and a sensor having an actuated and a non-actuated state, said closure being operatively coupled to said housing and adapted to be pivoted between an open and a closed position relative to said housing;
    said tubing section is adapted to be received about said rotor and said first mounting member is receivable in a predetermined position within the at least one recess of said housing; and
    said sensor is responsive to said at least a first mounting member of said fluid delivery set relative to said at least one recess of said housing for monitoring delivery of fluid through said infusion apparatus, wherein when said at least a first mounting member is in the predetermined position within said at least one recess, said closure when pivoted to the closed position relative to said housing is adapted to engage and displace a predetermined amount said at least a first mounting member in a first direction and into a secured position within said recess which causes a change in state of said sensor from the non-actuated to the actuated state, whereby subsequent displacement of said at least a first mounting member a predetermined amount from the secured position in a second or third direction substantially perpendicular the first direction causes a change in state of said sensor from the actuated to the non-actuated state, and whereby subsequent pivotal movement of the closure from the closed position to the open position results in displacement of said at least a first mounting member a predetermined mount from the secured position in a fourth direction generally opposite the first direction which causes a change in state of said sensor from the actuated to the non-actuated state.

13. A fluid delivery set according to claim 12, wherein said sensor comprises a biased sensing member, whereby said at least a first mounting member is adapted to compress said biased sensing member from a substantially extended position to a substantially retracted position as said closure is pivoted to the closed position which causes the change in state of said biased sensing member from the non-actuated to the actuated state.

14. A fluid delivery set according to claim 13, wherein said mounting member comprises a set adapter having a shoulder portion adapted for engaging and compressing said biased sensing member into the retracted position when said closure is pivoted to the closed position.

\* \* \* \* \*